United States Patent [19]

Venkateswaran et al.

[11] Patent Number: 4,937,074

[45] Date of Patent: Jun. 26, 1990

[54] METHOD OF TREATING RETROVIRUS INFECTION

[75] Inventors: Pinayur S. Venkateswaran, Chester; Irving Millman, Willow Grove; Baruch S. Blumberg, Philadelphia, all of Pa.

[73] Assignee: Fox Chase Cancer Center, Philadelphia, Pa.

[21] Appl. No.: 174,695

[22] Filed: Mar. 29, 1988

[51] Int. Cl.$^5$ .............................................. A61K 35/78
[52] U.S. Cl. .................................. 424/195.1; 514/885
[58] Field of Search ....................... 424/195.1; 514/885

[56] References Cited

U.S. PATENT DOCUMENTS 4,673,575  6/1987  Venkateswaran et al. ...... 424/195.1

OTHER PUBLICATIONS

Chopra et al., "Indigenous Plant of India", Dhur & Son, 1958, p. 519.
Nadkarni, "Indian Materia Medica", vol. 1, 3rd ed, pp. 948–949.
Steinmetz, Codex Vegetabilis, 1957, II 828.

Primary Examiner—John W. Rollins
Attorney, Agent, or Firm—Dann, Dorfman, Herrell & Skillman

[57] ABSTRACT

Method of treating retrovirus infection by administering extract of *Phyllanthus niruri*.

13 Claims, 2 Drawing Sheets

METHOD OF TREATING RETROVIRUS INFECTION

The present invention relates to treatment of retrovirus infection, and in particular to treatment of such infection by administering a component of *Phyllanthus niruri*, which has been found to have in vivo retroviral inhibitory activity.

*Phyllanthus niruri* Linn (*P. niruri*) is a herb common to central and southern India that has been used in ayurvedic medicine to treat a variety of maladies. For example, in Volume 1, "Doctor K. M. Nadkarni's Indian Materia Medica" (3rd Ed.; revised and enlarged by A. K. Nadkarni, p. 948), it is stated that the plant is considered de-obstruent, diuretic, astringent and cooling and formulations for the treatment of jaundice, as well as some forms of dropsy, gonorrhea, menorrhagia and other genitourinary affections of a similar type are described. It is further stated that the juice of the stem may be mixed with oil for use in ophthalmia and that the whole plant may be pounded with its root and combined with rice water to provide a poultice for ulcers, sores and swellings. A poultice of the leaves mixed with salt is purported to cure itch and other skin affections. A bitter neutral substance named "phyllanthin" has been isolated from the plant. As a stomachic bitter, it is said to be useful in dyspepsia. The plant is also said to be useful in treating diabetes.

Historically, there has been some confusion with the name *P. niruri*. For example, Muller (Argoviensis, DC. Prodr., 15 (2): 406, 1866) has interpreted that *P. niruri* is composed of six different varieties. Webster, (J. Arnold Arboretun, 38 (4):300, 1956), in a major revision of the genus Phyllanthus, separated *P. niruri* into a number of distinct species, belonging to a subgenus also called Phyllanthus. These are the species that are generally recognized today. However, practitioners of Ayurvedic medicine still use the name *P. niruri* to refer to certain similar species of Phyllanthus.

In the context of the present specification, *P. niruri* is used to refer to any species of Phyllanthus which, upon extraction, as described below, yield a fraction comprising a pharmacologically active agent that exhibits endogenous reverse transcriptase inhibitory activity. These plant species include, among others, *P. niruri* L., *P. amarus* (a species to 1which many older botanical records of *P. niruri* probably refer), *P. fraternus* and *P. asperulatus*.

In our U.S. patent application Ser. No. 727,452, filed Apr. 26, 1985, now U.S. Pat. No. 4,673,575, there is disclosed a composition extracted from *P. niruri*, a pharmaceutical preparation containing such composition and a method of using the pharmaceutical preparation for treating chronic hepatitis virus infection.

SUMMARY OF THE INVENTION

It has now been discovered that the *P. niruri* extract described in our aforesaid U.S. Pat. No 4,673,575, is effective in treating retrovirus infection. Hepatitis B virus and the related woodchuck hepatitis virus (WHV) and duck hepatitis virus (DHBV) all have similar replicative processes, one phase of which requires an endogenous reverse transcriptase. Our detailed analysis of the mechanism of inhibition of DHBV replication in vitro, in tissue culture studies by fractions of the extract of *P. niruri*, revealed that it is a strong inhibitor of reverse transcriptase and, therefore, it should be effective against retroviruses whose replication is dependent upon reverse transcription. The present invention derives from these and subsequent studies.

Thus, in accordance with the present invention, there is provided a method for treating retrovirus infection by administering a pharmaceutical preparation including, as an active ingredient, a component of *P. niruri* having endogenous reverse transcriptase inhibitory activity, in an amount effective to inhibit growth of the retrovirus. The active agent(s) is (are) recoverable using conventional extraction techniques and may be isolated by methanol extraction, as well as by aqueous extraction of the plant material.

The term "retrovirus" as used herein, refers to a class of viruses of vertebrate animals in which the genetic material is RNA, instead of DNA. Such viruses are accompanied by a polymerase enzyme known as "reverse transcriptase", which catalyzes transcription of viral RNA into double-stranded DNA. The resultant DNA may remain in a dormant state in an infected cell for an indeterminate period of time, or become incorporated into the cells genome and actively cause the formation of new virions. Retroviruses may be oncogenic.

The synthesis of complimentary DNA from RNA templates, under the control of reverse transcriptase, is the reverse of the usual mechanism involved in viral replication, wherein RNA copies are transcribed from DNA sequences; hence the name reverse transcriptase.

Various retroviruses may be treated using the method of the invention including, but not limited to, Rous sarcoma virus, Moloney murine leukemia virus, Human T cell Leukemia Virus (HTLV I and HTLV II) and human immunodeficiency virus (HIV-I and HIV-II), the latter including the etiologic agent of acquired immunodeficiency syndrome (AIDS).

While a concerted effort is being made to develop effective drug therapy for retrovirus infection, especially for treatment of AIDS, only limited progress has been made to date. Some of the candidate drugs that have demonstrated effectiveness, such as azidothymidine (AZT) and foscarnet (trisodium phosphonoformate) have toxic side-effects that many patients cannot tolerate. Tests conducted using the above-described extract of *P. niruri* against retrovirus infection, by contrast, have shown that the extract is effective in prolonging the survival time of infected animals, with no evidence of toxicity/to treated animals or to human lymphocytes in tissue culture.

BRIEF DESCRIPTION OF THE DRAWINGS

Referring to the drawings herein.

DETAILED DESCRIPTION OF THE INVENTION

The extract of P. niruri having anti-retroviral activity may be obtained in the manner generally described in our U.S. Pat. No. 4,673,575, the entire disclosure of which is incorporated by reference in the present application, as if set forth herein in full. According to the extraction procedure there described, dry, powdered, plant material, preferably from the whole plant, i e., stems, leaves and roots, is extracted with hexane, and the hexane extract and residue are separated. The hexane extract is concentrated to promote crystallization of crystallizable components and the crystallized product is separated from the supernatant. Soluble fractions in the supernatant are separated chromatographically. The residue of the hexane extract undergoes extraction with benzene and the benzene extract and residue are separated. The soluble fractions of the benzene extract are separated chromatographically.

Figure 1:
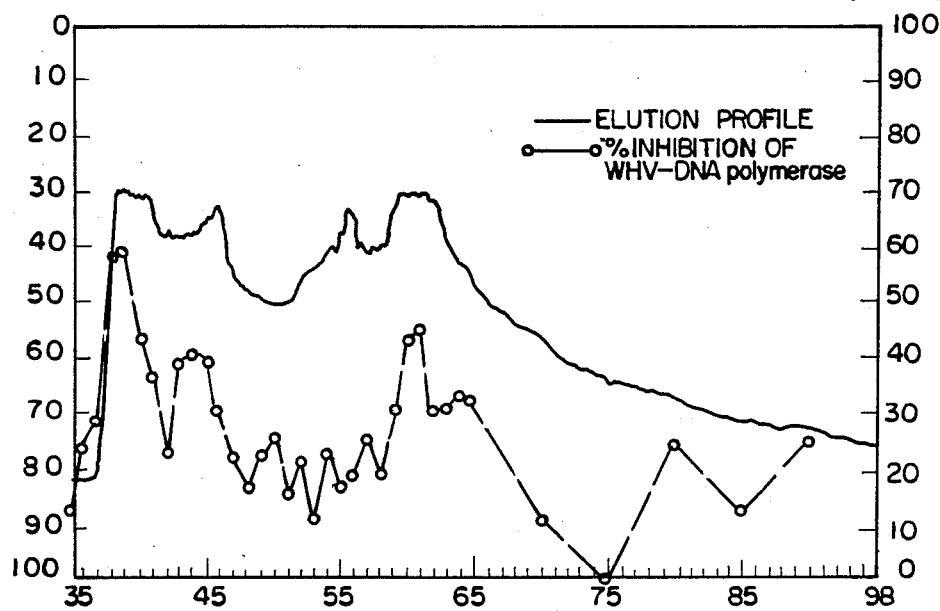
FIG. 1 shows the elution profile (absorbance at 280 nm) of an aqueous extract of *P. niruri* (whole plant) from a Sephadex G-10 column eluted with distilled water, which is represented by the solid line. The percent inhibition of WHV-DNA polymerase given by each fraction from the G-10 column is represented by the broken line.

The residue after benzene extraction is further extracted with methanol and the methanol extract is separated from the residue. The methanol extract is processed in the same general manner as the hexane extract and results in crystallized product and fractions which are thereafter chromatographically separated from the supernatant. The residue after the methanol extraction is subjected to aqueous extraction and the aqueous extract is separated. The methanol extract exhibits significant HBV-DNA polymerase inhibitory activity. If desired, the extract of P. niruri may be prepared using fresh plant material Alternatively, an aqueous extract of the whole plant may be fractionated using chromatographic techniques. For example, fractionation of an aqueous extract of P. niruri (whole plant) has been carried out using a Sephadex G-10 column. The results of such a fractionation are shown in FIG. 1. The continuous solid line represents the elution profile of the aqueous extract. The broken line represents the percentage of inhibition of woodchuck hepatitis virus WHV DNA polymerase produced by the various fractions. As can be seen from FIG. 1, DNA polymerase inhibitory activity is greatest in fractions 39 (containing components whose molecular weight (MW) is higher than 1,000 daltons), 45 (approx. MW 700 daltons), and 61 (approx. MW 350 daltons).

Figure 2:
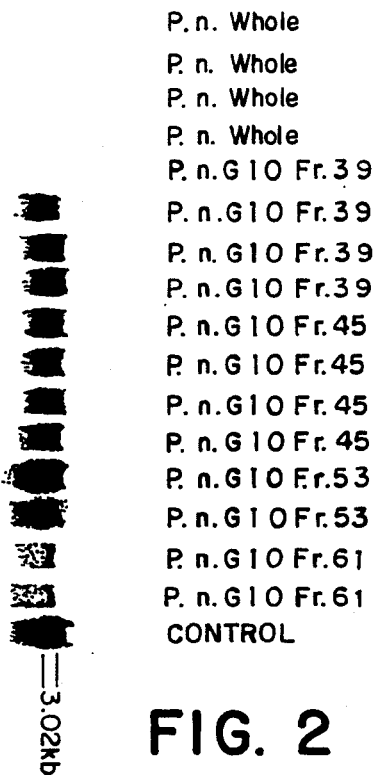
FIG. 2 shows an autoradiographic pattern resulting from an analysis of duck hepatitis virus (DHBV)-DNA polymerase inhibitory effect of the fractions obtained from the Sephadex G-10 column (as shown in FIG. 1) having the greatest inhibitory activity with respect to WHV-DNA polymerase.

FIG. 2 represents an autoradiograph showing the duck hepatitis virus (DHBV) DNA polymerase inhibitory effect of fractions, 39, 45, 53 and 61, recovered from the Sephadex G-10 column, as well as that of the unfractionated whole plant extract. This pattern indicates that fraction 61 has the greatest relative DNA polymerase inhibitory activity, as indicated by the faintness of the band at 3.02 kb, representing DHBV DNA.

The fractions recovered by chromatographic separation of the aqueous extract of P. niruri may be further purified using procedures familiar to those skilled in the art, such as HPLC.

Although the mechanism responsible for the observed anti-retroviral activity has not been elucidated, it is believed that the active agent present in the P. niruri extract inhibits retrovirus replication by inhibiting reverse transcriptase.

The pharmaceutical preparation comprising the fraction of P. Niruri having anti-retroviral activity may be conveniently formulated for administration with a biologically acceptable medium such as water, buffered saline, polyol (for example, glycerol, propylene glycol, liquid polyethylene glycol and the like) or suitable mixtures thereof. The concentration of the active ingredients in the chosen medium should normally be from about 15 mg/ml to about 50 mg/ml. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the active ingredient of P. niruri, its use in the pharmaceutical preparation is contemplated.

Supplementary active ingredients, such as other antiviral agents or immune modulators, or both, can also be incorporated into the pharmaceutical preparation, if necessary or desirable. Such supplementary active ingredients may include, for example, zidovudine (AZT), foscarnet, trimetrexate, 2',3'-dideoxycytidine (DDC), ganciclovir, o-interferon, interleukin-2, ampligen, isoprinosine, and the like.

It is especially advantageous to formulate the pharmaceutical preparation in dosage unit form for ease of administration and uniformity of dosage. Dosage unit form as used herein refers to a physically discrete unit of the pharmaceutical preparation appropriate for the patient undergoing treatment. Each dosage should contain the quantity of active ingredient calculated to produce the desired therapeutic effect in association with the selected pharmaceutical carrier. Procedures for determining the appropriate dosage unit for inhibiting or suppressing infectivity of retrovirus in a given class of patient are well known to those skilled in art.

Generally, patients having a retrovirus infection are administered a dosage containing from about 5 to about 20 mg. of the active components of the P. niruri extract per kilogram of body weight per day. This dosage range should be satisfactory for producing the desired anti-retroviral effect in humans, as indicated by a significant drop in the virus titre The pharmaceutical preparation is preferably administered parenterally, e.g., intravenously or intraperitoneally, in the form of a dosage unit. Other modes of administration may also be effective, such as oral administration.

The pharmaceutical preparation may be administered at appropriate intervals, for example, once a day until the virus titre drops (approximately two (2) orders of magnitude), after which the dosage is reduced to a maintenance level of once a week. The appropriate interval in a particular case would normally depend on the condition of the patient. As used herein, the term "patient" includes both humans and animals.

Of course, the methanol must be removed from the active component before adminstration to a patient. This may conveniently be done by evaporating the methanol in vacuo and redissolving the methanol-free residue in biological medium, such as PBS.

The following examples are provided to describe the invention in further detail. These examples are intended to illustrate and not to limit the invention.

EXAMPLE 1

Inhibition of Rous Sarcoma Virus Reverse Transcriptase In Vitro Using Aqueous Extract Of P. niruri The inhibitory effect of P. niruri extract (fraction 61, see FIGS. 1 and 2) on reverse transcriptase (RT) of Rous Sarcome virus (RSV) was determined by the following assay procedure which utilizes the incorporation of radiolabeled nucleotide ($^3$H-dTTP) into TCA-precipitable DNA as a measure of reverse transcriptase activity Tissue culture fluids containing RSV reverse transcriptase activity were diluted tenfold with 50 mM Tris-HCl, pH 8.3, and 20 µl of the diluted culture fluid was used as the enzyme source to which was added 20 µl of P. niruri extract followed by 100 µl of a mixture of Tris-HCl (50 mM), KCl (80 mM), $MgCl_2$ (6 mM), DTT (10 mM), dATP, dGTP, dCTP (2 mM each), dTTP (60 mCi/mmole; 20 mM), Triton X100 (0.5% 20 µl) and oligo $(rA)_n(dT)_{10}$ (0.5 µg/10 µl). Samples were incubated at 37° C. for 30 min. The reaction was terminated by the addition of 2.5 ml of 5% TCA (containing 2% pyrophosphate). Then 40 µl of 2.5% BSA and 100 µl of 0.5% calf thymus DNA were added as carriers, and the mixture was filtered through a glass fiber filter (Whatman). The filter was washed thrice with 5% TCA containing pyrophosphate and thrice with 95% ethanol, dried under a heat lamp, and the radioactivity remaining on the filter was determined in a scintillation counter. Assay tubes containing Tris-HCl, pH 8.3, instead of culture fluid containing reverse transcriptase activity, were used as controls for enzymatic reaction and tubes omitting only the extract as controls for the inhibitor.

Figure 3:
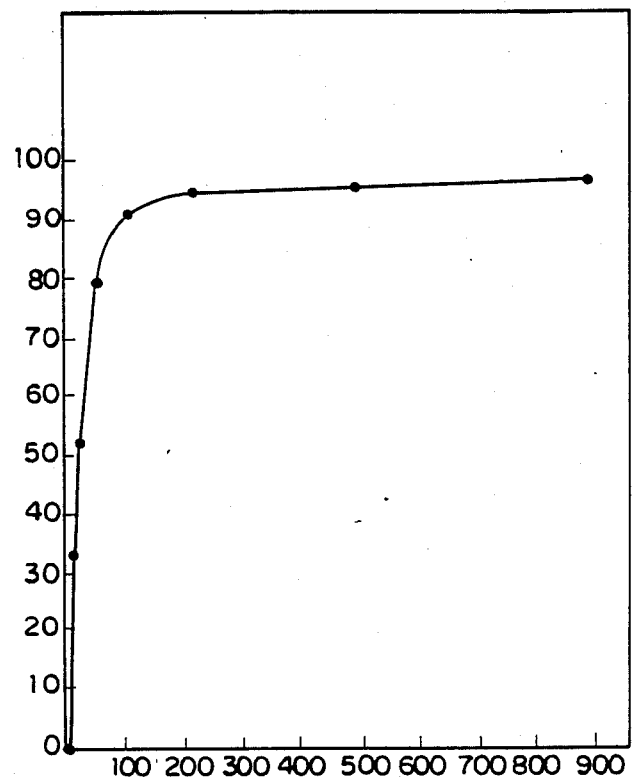
FIG. 3 graphically represents percent inhibition (ordinate) of Rous sarcoma virus determined in vitro as a function of concentration of *P. niruri* extract (μg/ml) (abscissa)

The inhibition of RSY RT by aqueous extract of P. niruri (P. amarus) is graphically represented in FIG. 3. From FIG. 3 it can be seen that the increase in inhibition is linear with increasing concentration of the extract up to 60 µg/ml at which point the inhibition reaches over 80%.

EXAMPLE 2

Inhibition Of Moloney Murine Leukemia Virus Reverse Transcriptase In Vitro Using Aqueous Extract Of P. niruri Essentially the same assay as described in Example 1 was used for determining the inhibitory effect of P. niruri extract (fraction 61; see FIGS. 1 and 2) on Moloney murine leukemia virus (MoMLV) RT. The metal ion requirement for MoMLV RT is manganese Accordingly, $MgCl_2$ should be replaced with $MnCl_2$ (or an equivalent) in performing the assay.

Figure 4:
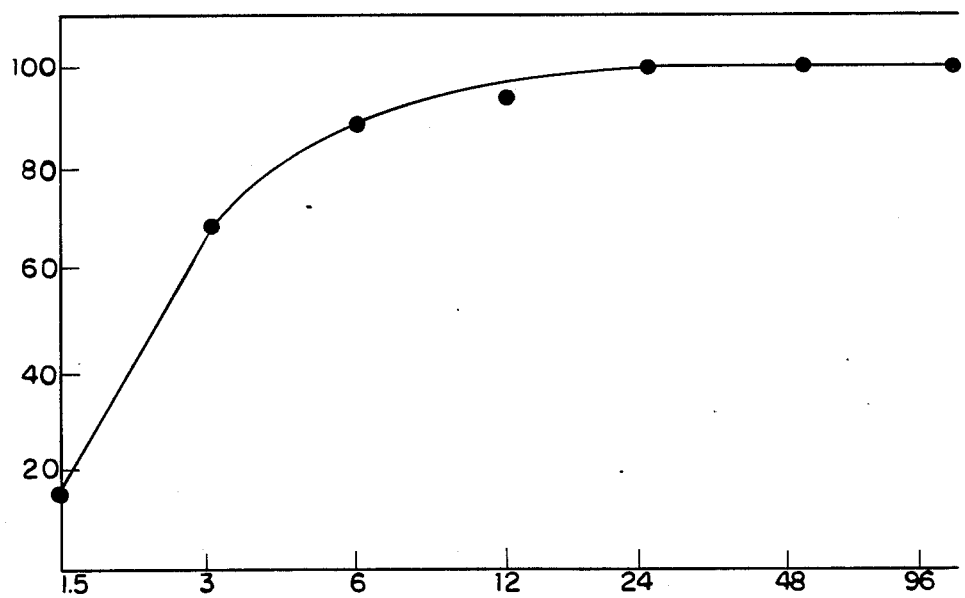
FIG. 4 graphically represents percent inhibition (ordinate) of Moloney murine lukemia virus determined in vitro as a function of concentration of P. niruri extract (μg/ml) (abscissa).

The inhibition of MoMLV RT by aqueous extract of P. niruri (P. amarus) is graphically represented in FIG. 4.

As can be seen in FIG. 4, MoMLV RT is more sensitive to the extract than RSV RT. The inhibition is linear with concentration up to 6 µg/ml, at which point the inhibition is greater than 80%

EXAMPLE 3

Inhibition of Human Immunodeficiency Virus Reverse Transcriptase In vitro Using Aqueous Extract of P. niruri Inhibition of HIV reverse transcriptase activity was determined using Triton X100-activated lysates of polyethylene glycol concentrated HIV (HTLV-III). The assay procedure is identical to that described for RSV RT and MoMLv RT. The inhibition (%) of the HIV RT by P. niruri (P. amarus) extract is given below in Table 1.

TABLE 1

| Concentration of Phyllanthus Extract | CPM RT Activity | % Inhibition |
| --- | --- | --- |
| 0 [control] | 57,900 | — |
| 0.5 µg/ml | 49,940 | 14 |
| 5.0 µg/ml | 51,270 | 11 |
| 50.00 µg/ml | 23,885 | 59 |
| 500.0 µg/ml | 2,570 | 96 |

EXAMPLE 4

Anti-HIV Activity In Infection Assays

HIV was prepared from a conditioned culture fluid of a CEM cell line (ATCC CCL 119) infected with HIV. The cell line is described in 18 Cancer 522 (1965); see also: 19 Cancer 1725 (1966) and 40 Exp. Cell Res. 197 (1965). The culture fluid was clarified of cells by low speed centrifugation (900xg) and filtration through 0.45µ filter and was used to infect cultures of C3 lymphocytea in the presence of P. niruri (P. amarus) extract at 50 and 500 µg/ml concentration. It was previously determined that the extract was non-toxic to these cells at these concentrations. Fraction 61 from Sephadex G10 (see FIG. 1) was also tested at a concentration of 30 µg/ml for its effect on HIV infection of C3 lymphocytes. C3 lymphocyte target cells were incubated in the presence of the virus and the inhibitor for 24 hours. Inhibitors and unabsorbed virus were then removed by replacing the media with fresh growth medium and incubating the cultures. Infections were monitored by Indirect Immunofluorescence. The results of the assay are reported below in Table 2.

TABLE 2

Effect of P. niruri extract in an HIV infection assay.

| Inhibitor | Concentration | % IIF* Positive Cells | | | |
| --- | --- | --- | --- | --- | --- |
| | | 3 Days | 5 Days | 8 Days | 10 Days |
| None | — | 100 | — | — | — |
| P. nururi Extract | 500 µg/ml | 0 | 0 | 0 | <1 |
| P. niruri Extract | 50 µg/ml | <1 | <1 | 1 | 30 |
| P. niruri Sephadex G10 Fraction 61 | 30 µg/ml | 0 | 0 | 0 | 0 |

*IIF = Indirect Immunofluorescence

EXAMPLE 5

Inhibition of The Effect Of The Virus MoMLV in vivo Using Aqueous Extract Of P. niruri Six litters of Long-Evans rats were selected as test subjects and injected with 0.2 ml, containing $5 \times 10^5$ plaque forming units of Moloney murine leukemia virus, i.p. within 24 hours of birth.

Five days after birth, each litter was divided into a treatment group and a control group. Whenever a litter had an odd number, the additional test subject was placed in the treatment group. The treated animals had the lower portion (no more than one-half) of their tails removed, to distinguish these from the controls in each litter.

The tests animals in the treatment groups and control groups were weighed twice a week. The control test animals received 0.1 ml of 0.02 M KPO$_4$ buffered saline pH 7.4, i.p. twice a week. The test animals in the treatment groups received 0.1 ml of 1-8 dilution of P. niruri (18 mg/ml solution) i.p. twice a week for one week. During the second week the test subjects in the treatment group received a 1-4 dilution of P. niruri for their first dose and a 1-2 dilution for their second dose. The change in dosage was due to concern about toxicity in new born test subjects. The dosage was increased once no toxic effect was noted. By the third week, those in the treatment group received undiluted P. niruri twice a week.

The test animals remained with their mothers and the weighings and injections continued for both the treatment and control groups twice a week until they were six weeks old. At that time the test subjects were toe clipped for identification and separated according to sex and litter. Males were housed two to a cage; and females no more than four to a cage. The injections continued twice a week but the weighings were reduced to one a week, and the weight of each test subject was recorded.

Throughout the course of the study, the animals were checked every working day. Any animal found dead was examined for signs of tumor. At 28 weeks of age, thirty one of the sixty test subjects involved remained alive. Of the thirty one living test animals, nineteen were in treatment groups and twelve were in control groups.

After 30 weeks, there were thirteen surviving test animals, of which eleven were in treatment groups and only two were in control groups.

The treated animals, on average, survived longer than the untreated animals, indicating a significant effect of treatment with P. niruri extract (P=0.02).

While certain preferred embodiments of the present invention have been described above, it is not intended to limit the invention to such embodiments, but various modifications may be made thereto, without departing from the scope and spirit of the present invention, as set forth in the following claims.

What is claimed is:

1. A method for treating patients having a retrovirus infection, which comprises administering to said patients a pharmaceutical preparation comprising, as an active ingredient, a component of *Phyllanthus niruri* having endogenous reverse transcriptase inhibitory activity, in an amount effective to inhibit infectivity of said retrovirus.

2. A method as claimed in claim 1, wherein said pharmaceutical preparation is administered in doses containing from about 5 to about 20 mg. of said active ingredient/kg. of patient body weight per day.

3. A method as claimed in claim 1, wherein said pharmaceutical preparation is administered in combination with a biologically acceptable medium.

4. A method as claimed in claim 3, wherein said pharmaceutical preparation is administered in combination with a biologically acceptable medium at a concentration of about 15 to about 50 mg. of said active ingredient/ml. of medium.

5. A method as claimed in claim 1, wherein the pharmaceutical preparation is administered parenterally.

6. A method as claimed in claim 5, wherein the pharmaceutical preparation is administered intraveneously.

7. A method as claimed in claim 5, wherein the pharmaceutical preparation is administered intraperitoneally.

8. A method as claimed in claim 1, wherein the pharmaceutical preparation is administered orally.

9. A method as claimed in claim 1, wherein said retrovirus is selected from the group consisting of Rous sarcoma virus, Moloney murine leukemia virus and human immunodeficiency virus.

10. A method as claimed in claim 1 wherein said pharmaceutical preparation is administered in combination with a supplemental antiviral agent, an immune modulator, or a combination thereof.

11. A method for prolonging the survival of patients infected with human immunodeficiency virus (HIV) by administering to said patients a pharmaceutical preparation comprising, as an active ingredient, a component of *Phyllanthus niruri*, obtainable by methanol or water extraction, said component having endogenous reverse transcriptase inhibitory activity, in an amount effective to inhibit the infectivity of said virus.

12. A method as claimed in claim 11, wherein said pharmaceutical preparation is administered in doses containing from about 5 to about 20 mg. of said active ingredient/kg. of patient body weight per day.

13. A method as claimed in claim 11, wherein said pharmaceutical preparation is administered in combination with a supplemental antiviral agent, an immune modulator, or a combination thereof.

* * * * *

UNITED STATES PATENT AND TRADEMARK OFFICE
CERTIFICATE OF CORRECTION

PATENT NO. : 4,937,074

DATED : June 26, 1990

INVENTOR(S) : Pinayur S. Venkateswaran, Irving Millman and Baruch S. Blumberg

It is certified that error appears in the above-identified patent and that said Letters Patent is hereby corrected as shown below:

Column 1, line 47, before "which" delete --1--.

Column 2, line 33, change "HIY-II" to --HIV-II--.

Column 2, line 47, after "toxicity" delete --/--.

Column 4, line 25, change "o-interferon" to --α-interferon--.

Column 5, line 36, change "RSY" to --RSV--.

Column 6, lines 26-27, change "lymphocytea" to --lymphocytes--.

Column 7, line 6, after "in" delete --'--.

Signed and Sealed this

Seventeenth Day of December, 1991

Attest:

HARRY F. MANBECK, JR.

*Attesting Officer*      *Commissioner of Patents and Trademarks*

UNITED STATES PATENT AND TRADEMARK OFFICE
CERTIFICATE OF CORRECTION

PATENT NO. : 4,937,074

DATED : June 26, 1990

INVENTOR(S) : Pinayur S. Venkateswaran, Irving Millman and Baruch S. Blumberg

It is certified that error appears in the above-identified patent and that said Letters Patent is hereby corrected as shown below:

Column 1, after the title of the invention, insert the following
   paragraph:
      -- Pursuant to 35 U.S.C. §202(c), it is hereby acknowledged
   that the U.S. Government has certain rights in the invention
   described herein, which was made in part with funds from the
   National Institutes of Health.--

Signed and Sealed this

Seventeenth Day of November, 1992

Attest:

DOUGLAS B. COMER

Attesting Officer

Acting Commissioner of Patents and Trademarks